(12) United States Patent
Lee et al.

(10) Patent No.: US 8,047,077 B2
(45) Date of Patent: Nov. 1, 2011

(54) SURFACE ACOUSTIC WAVE SENSOR AND SENSING METHOD USING SURFACE ACOUSTIC WAVE

(75) Inventors: Hun Joo Lee, Seoul (KR); Soo Suk Lee, Suwon-si (KR); Soo Hyung Choi, Seoul (KR)

(73) Assignee: Samsung Electronics Co., Ltd. (KR)

( * ) Notice: Subject to any disclaimer, the term of this patent is extended or adjusted under 35 U.S.C. 154(b) by 411 days.

(21) Appl. No.: 12/404,595

(22) Filed: Mar. 16, 2009

(65) Prior Publication Data
US 2010/0231308 A1 Sep. 16, 2010

(51) Int. Cl.
*G01N 29/36* (2006.01)
*H02N 2/00* (2006.01)

(52) U.S. Cl. ............ 73/579; 73/597; 73/657; 310/313 B
(58) Field of Classification Search ............... 73/579, 73/597, 598, 657; 310/313 B
See application file for complete search history.

(56) References Cited

U.S. PATENT DOCUMENTS

| | | | |
|---|---|---|---|
| 7,002,281 B2 * | 2/2006 | Andle | 310/313 B |
| 7,047,792 B1 * | 5/2006 | Bhethanabotla et al. | 73/24.01 |
| 7,205,701 B2 * | 4/2007 | Liu et al. | 310/313 R |
| 7,301,852 B2 * | 11/2007 | Leggett et al. | 367/32 |
| 7,463,551 B2 * | 12/2008 | Leggett et al. | 367/32 |
| 7,816,837 B2 * | 10/2010 | Fujimoto et al. | 310/313 D |
| 2005/0056098 A1 | 3/2005 | Solie | |

FOREIGN PATENT DOCUMENTS

| KR | 1020050068940 A | 7/2005 |
|---|---|---|
| KR | 1020060127936 A | 12/2006 |

* cited by examiner

*Primary Examiner* — J M Saint Surin
(74) *Attorney, Agent, or Firm* — Cantor Colburn LLP (57) ABSTRACT

A surface acoustic wave ("SAW") sensor includes; a first signal generator which generates a first signal having a predetermined frequency bandwidth using a pseudo random sequence, a second signal generator which generates a second signal with a predetermined frequency, a signal blender which blends the first signal with the second signal to generate a blended signal having the predetermined frequency bandwidth with the predetermined frequency as a center frequency, a wave generator which generates a surface acoustic wave using the blended signal, which converts the surface acoustic wave into a third signal after the surface acoustic wave travels a predetermined distance, and which outputs the third signal, and a signal detector which detects a change in the third signal from the wave generator to sense a substance bound to the wave generator.

8 Claims, 6 Drawing Sheets

SURFACE ACOUSTIC WAVE SENSOR AND SENSING METHOD USING SURFACE ACOUSTIC WAVE

BACKGROUND

1. Field

Exemplary embodiments relate to a surface acoustic wave ("SAW") sensor and a sensing method using a SAW.

2. Description of the Related Art

In a SAW sensor using a piezoelectric material, a SAW may be created when a radio frequency ("RF") signal is applied to an input electrode. If a target substance is bonded to the surface of the SAW sensor, the surface mass of the SAW sensor may change. The SAW may be subjected to a change due to the weight of the target substance on the SAW sensor. The SAW may be converted again into an electrical signal and outputted from an output electrode. After the SAW is converted back into an electrical signal, the SAW sensor may detect a change in the output signal caused by the target substance to sense the substance bonded to the sensor.

One technique used for applying a signal to an electrode of the SAW sensor for generating a SAW makes use of oscillation which applies an output signal output from a SAW sensor as an input signal back to the SAW sensor. This technique requires a gap between an input electrode and an output electrode that is relatively narrow and every sensor oscillates independently when a plurality of SAW sensors is employed. Another technique adopts a network analyzer to generate a signal of a predetermined frequency on the outside of a SAW sensor and applies the signal to the SAW sensor. The signal applied by the network analyzer may have a frequency separation of several kHz or greater.

SUMMARY

Exemplary embodiments provide a SAW sensor having improved resolution, capable of generating a signal having a wide frequency bandwidth with respect to a center frequency of a SAW element using a pseudo random sequence to apply the generated signal to the SAW element, and a sensing method using a SAW.

An exemplary embodiment provides a SAW sensor. The SAW sensor may include: a first signal generator generating a first signal having a predetermined frequency bandwidth using a pseudo random sequence; a second signal generator generating a second signal with a predetermined frequency; a signal blender blending the first signal with the second signal to generate a blended signal having the predetermined frequency bandwidth with the predetermined frequency of the second signal as a center frequency; a wave generator generating a SAW using the blended signal, converting the SAW into a third signal after the SAW travels a predetermined distance, and outputting the third signal; and a signal detector detecting a change in the third signal from the wave generator to sense a substance bound onto the wave generator.

Another exemplary embodiment provides a sensing method using a SAW. The sensing method using a SAW may include: generating a first signal having a predetermined frequency bandwidth using a pseudo random sequence; generating a second signal with a predetermined frequency; blending the first signal with the second signal to generate a blended signal having the predetermined frequency bandwidth with the predetermined frequency of the second signal as a center frequency; generating a SAW using the blended signal in a wave generator, converting the SAW into a third signal after the SAW travels a predetermined distance, and outputting the third signal; and detecting a change in the third signal from the wave generator to sense a substance bound onto the wave generator.

BRIEF DESCRIPTION OF THE DRAWINGS

The above and other aspects, features and advantages of exemplary embodiments may be better appreciated in view of the following detailed description in conjunction with the accompanying drawings, in which.

DETAILED DESCRIPTION

The invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments of the present invention are described herein with reference to cross section illustrations that are schematic illustrations of idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present invention.

Hereinafter, the present invention will be described in detail with reference to the accompanying drawings.

Figure 1:
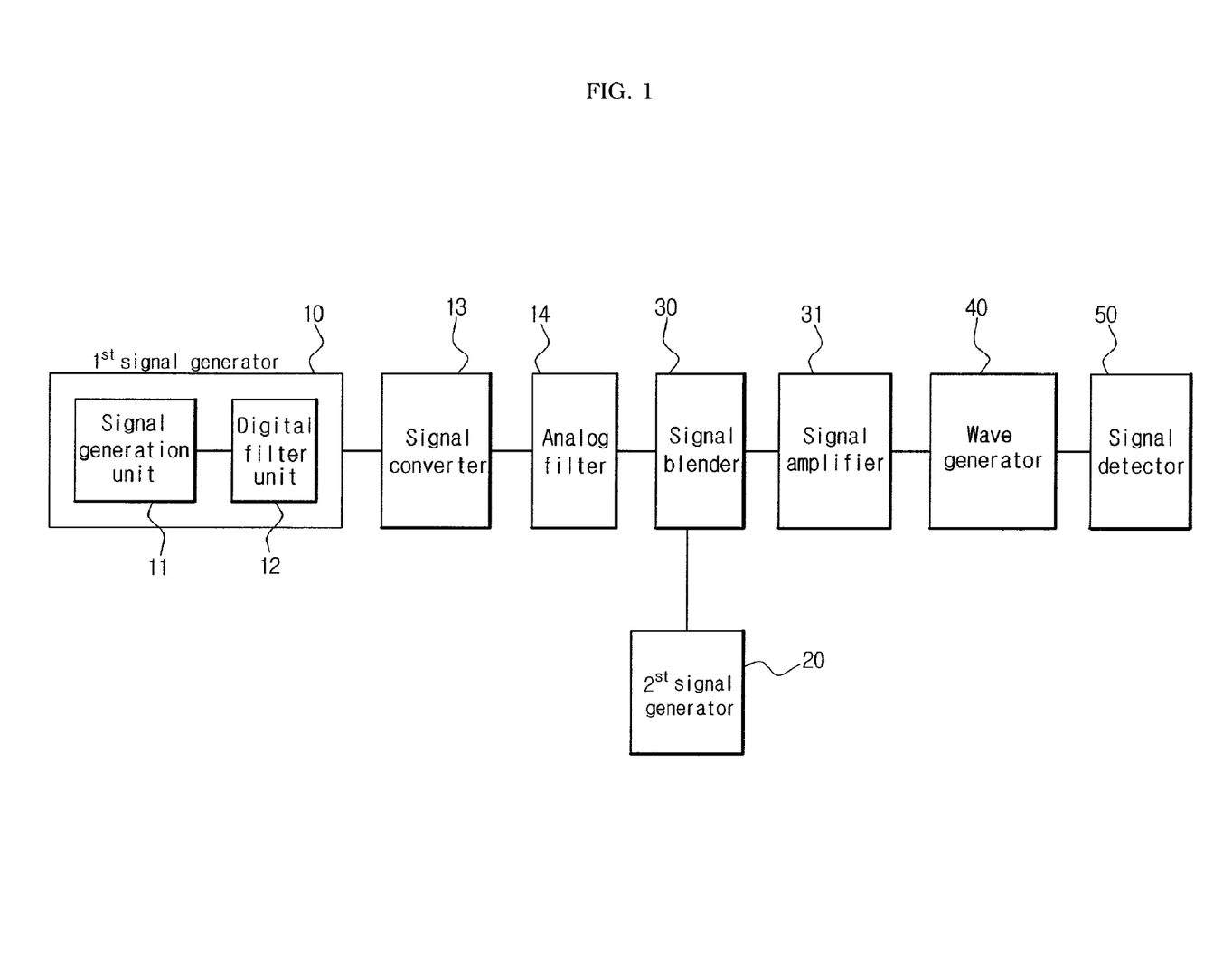
FIG. 1 is a schematic block diagram of an exemplary embodiment of a surface acoustic wave ("SAW") sensor.

FIG. 1 is a schematic block diagram of an exemplary embodiment of a surface acoustic wave ("SAW") sensor.

Referring to FIG. 1, the SAW sensor may include first and second signal generators 10 and 20, a signal blender 30, a wave generator 40 and a signal detector 50.

The first signal generator 10 may generate a first signal having a wide frequency bandwidth. Referring to FIG. 1, in one exemplary embodiment, the first signal generator 10 may include a signal generation unit 11 and a digital filter unit 12. In one exemplary embodiment, the signal generation unit 11 may use a pseudo random sequence generator to generate a first signal which is a digital signal, although alternative exemplary embodiments may utilize other methods of generating the first signal. The digital filter unit 12 may remove a noise signal from the first signal generated by the signal generation unit 11, wherein the noise signal exists in a frequency bandwidth other than a desired frequency bandwidth.

In FIG. 1, the SAW sensor may include a signal converter 13 connected to the first signal generator 10, and an analog filter 14. The signal converter 13 may convert the filtered first signal, which is a digital signal generated by the first signal generator 10 as described above, into an analog signal applicable to the SAW element. The analog filter 14 may remove a noise signal in a frequency bandwidth other than a desired frequency bandwidth from the analog signal output from the signal converter 13. Exemplary embodiments of the analog filter 14 may include a variety of filters, e.g., a band-pass filter or a low-pass filter to remove the noise signal. According to an exemplary embodiment, the analog filter 14 may be a SAW filter using SAW elements.

The second signal generator 20 may generate a second signal with a single frequency corresponding to a center frequency of the wave generator 40. That is, the frequency of the second signal may correspond to a frequency of a highest amplitude for an output signal of the wave generator 40 when no substance is bound onto the wave generator 40.

The signal blender 30 may blend the first signal generated by the first signal generator 10, which has been modified through the digital-to-analog ("D/A") conversion and noise signal filtering operations, with the second signal generated by the second signal generator 20. The blended signal thus obtained may have the second signal frequency as its center frequency and have the frequency bandwidth of the modified first signal. When the frequency of the first signal is out of the frequency domain of an output signal from the wave generator 40, it may be difficult to analyze a target substance by detecting the output signal. Therefore, the second signal with a frequency corresponding to the center frequency of the wave generator 40 may be used to adjust the frequency of a signal applied to the wave generator 40 to fall within a desired frequency bandwidth.

For instance, in an exemplary embodiment wherein the second signal has a frequency of 200 MHz, and the bandwidth of the first signal is 20 MHz, the signal blender 30 may blend the first signal and the second signal to generate a blended signal which has a bandwidth of 20 MHz with 200 MHz as its center frequency.

The blended signal generated by the signal blender 30 may be applied to the wave generator 40 for generating a SAW. According to an exemplary embodiment, a signal amplifier 31 may be connected to the signal blender 30 so that the blended signal may be amplified to a suitable amplitude to be inputted to the wave generator 40.

The wave generator 40 may include a SAW element which generates a SAW using the blended signal from the signal amplifier 31. Although the exemplary embodiment shown in FIG. 1 illustrates a SAW sensor with one wave generator 40, in alternative exemplary embodiments the SAW sensor may include a plurality of wave generators 40. A SAW thus generated may travel along the surface of the wave generator 40. The frequency, phase and amplitude of the SAW may change depending on the presence or absence of a substance bound to the wave generator 40, and depending upon the physical characteristics of the bound substance, e.g., mass.

Figure 2A:
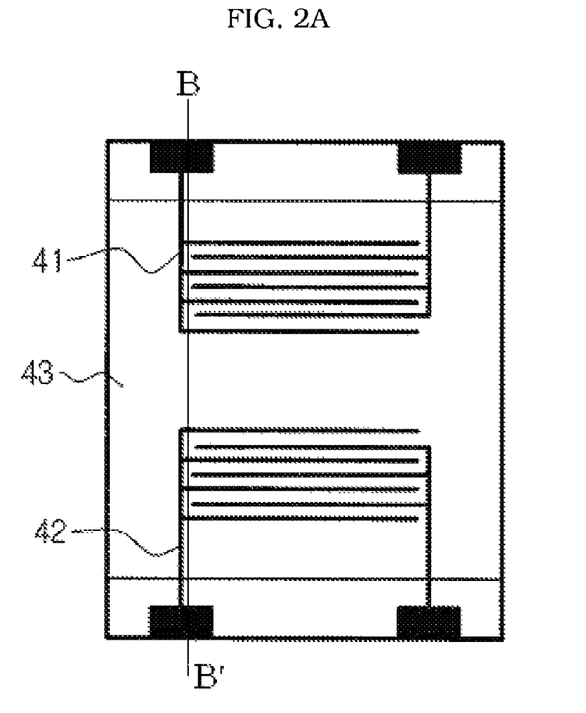
FIG. 2A is a top plan view illustrating an exemplary embodiment of a wave generator included in the exemplary embodiment of a SAW sensor of FIG. 1.
Figure 2B:
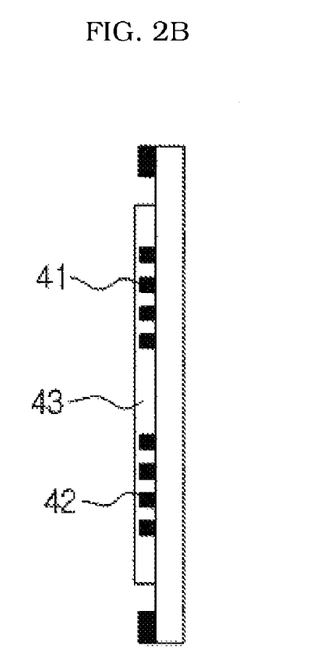
FIG. 2B is a cross-sectional view of the exemplary embodiment of a wave generator of FIG. 2A taken along line B-B'.

FIG. 2A is a top plan view illustrating an exemplary embodiment of a wave generator included in the exemplary embodiment of a SAW sensor of FIG. 1, and FIG. 2B is a cross-sectional view of the exemplary embodiment of a wave generator of FIG. 2A taken along line B-B'.

Referring to FIGS. 2A and 2B, the wave generator 40 may include an input unit 41, an output unit 42 and a reactor 43. According to an exemplary embodiment, the input unit 41 and the output unit 42 may be formed of interdigital transducers ("IDT"). The input unit 41 may convert an electrical signal inputted from the signal blender 30 into a SAW, which is a mechanical wave. The SAW may pass through the reactor 43 and may be propagated towards the output unit 42. The reactor 43 may be a region to which a target substance (not shown) for analysis is bonded. Depending on the kind of substance bonded to the reactor 43, the SAW traveling through the reactor 43 may exhibit different properties, e.g., the amplitude, phase, period, etc., may all be modified by the presence or kind of substance bound to the reactor. After passing through the reactor 43, the SAW may be propagated to the output unit 42 where it may be converted into an electric signal to be output from the output unit 42.

The signal detector 50 may detect an output signal from the wave generator 40, and sense a substance bonded to the reactor 43 of the wave generator 40 through the detected signal. For instance, when a target substance (not shown) is bound to the reactor 43 of the wave generator 40, the wave generator 40 may output a signal having a different center frequency, phase and/or signal amplitude. Therefore, the signal detector 50 may sense the presence of the substance on the wave generator 40 by such change and further, it may make quantitative and/or qualitative analysis of the target substance based on those changes.

Figure 3:
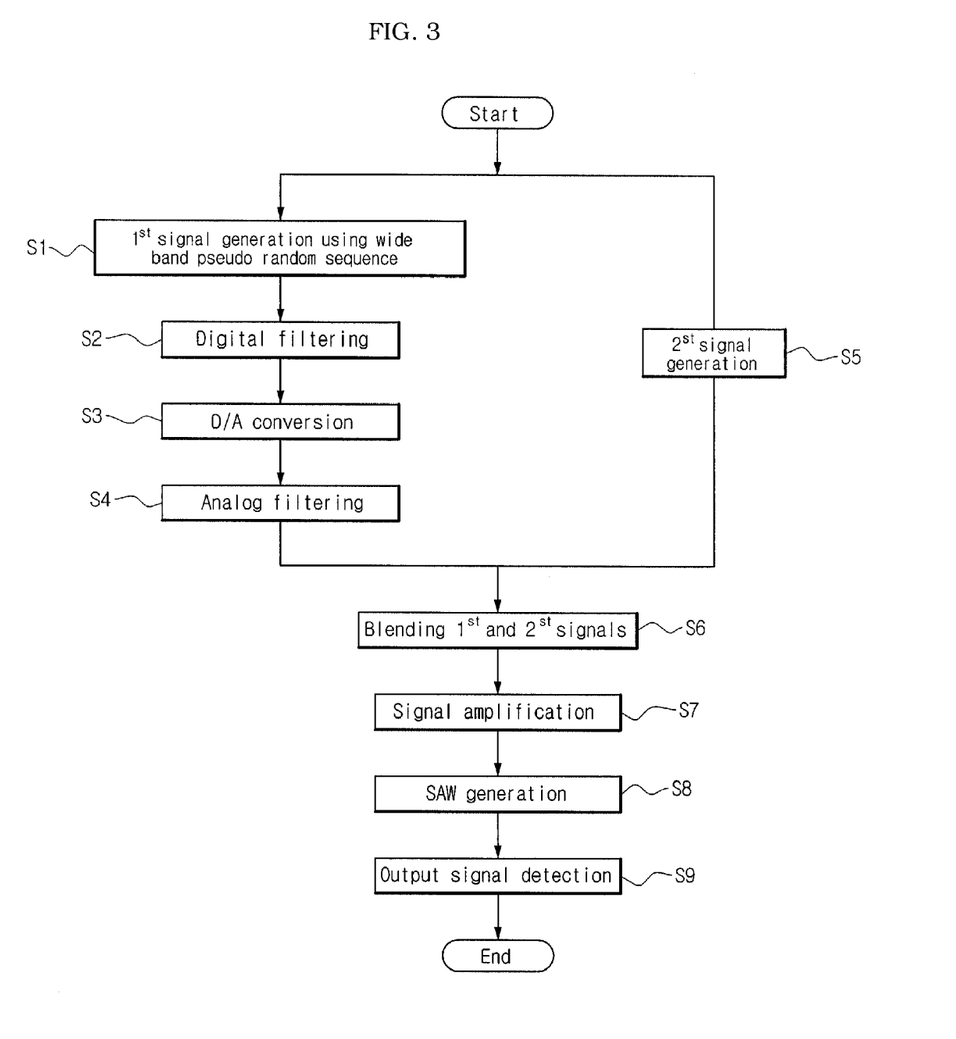
FIG. 3 is a flow chart illustrating each step of an exemplary embodiment of a sensing method using a SAW.

FIG. 3 is a flow chart illustrating each steps of an exemplary embodiment of a sensing method using a SAW.

Referring to FIG. 1 and FIG. 3, the sensing method using a SAW may include generating a first signal, which is a digital signal, using a pseudo random sequence in the first signal generator 10 (S1). The first signal may have a predetermined frequency bandwidth and may be generated by the signal generation unit 11 of the first signal generator 10. In FIG. 3, the signal generated by the signal generation unit 11 may be subjected to a filtering operation carried out in the digital filter unit 12 to remove a noise signal therein (S2).

Because the signal generation unit 11 may generate a digital signal using a pseudo noise sequence, the first signal may be converted into an analog signal to be input to a SAW element. As such, the signal converter 13 connected to the first signal generation unit 11 may convert the first signal into an analog signal (S3). Next, the analog filter 14 may remove a noise signal from the analog signal forwarded from the signal converter 13 (S4).

Figure 4A:
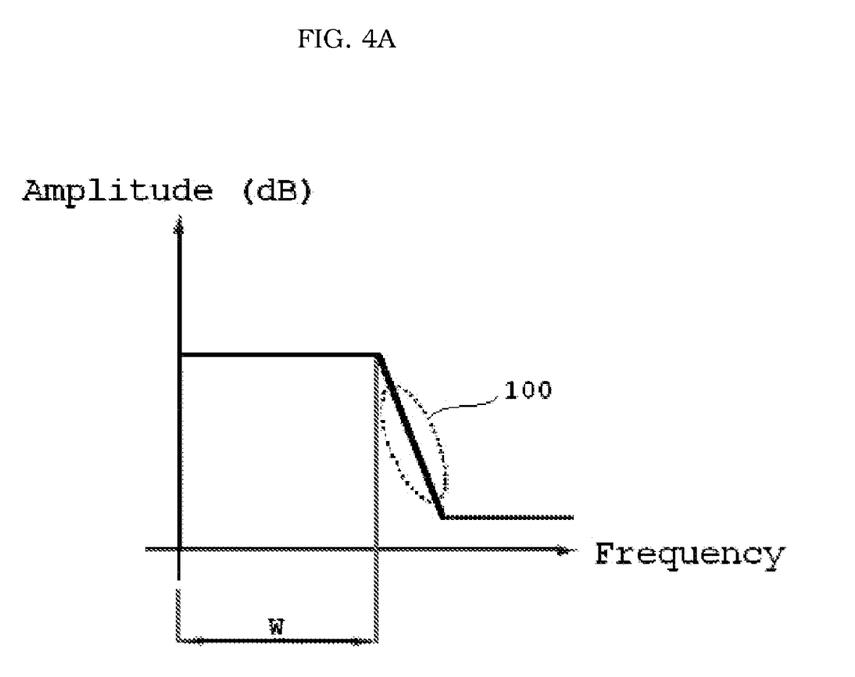
FIGS. 4A-4D are graphs illustrating exemplary embodiments of signal waveforms generated in an exemplary embodiment of a SAW sensor.
Figure 4B:
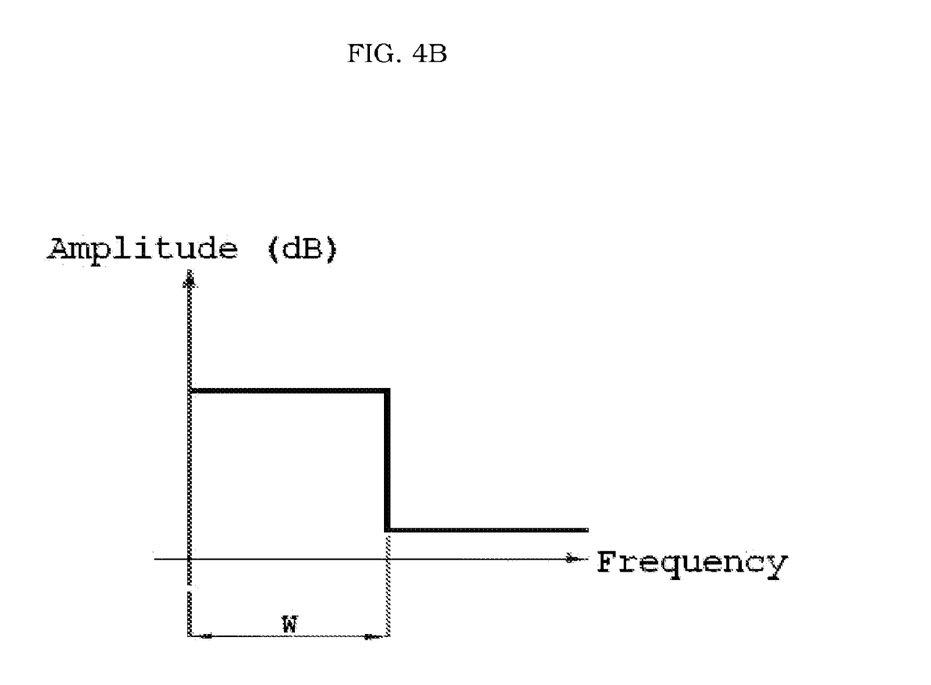

FIGS. 4A-D are graphs illustrating exemplary embodiments of signal waveforms generated in an exemplary embodiment of a SAW sensor. FIG. 4A illustrates the waveform of a first signal having gone through the D/A conversion in the signal converter 13. As illustrated, the first signal may have a substantially constant amplitude over a predetermined bandwidth W. However, the first signal may also have a noise signal 100 extending beyond the predetermined bandwidth W. FIG. 4B illustrates a first signal with noise signals removed by the analog filter 14. That is, a noise signal that existed outside the bandwidth W may be removed from the first signal.

Figure 4C:
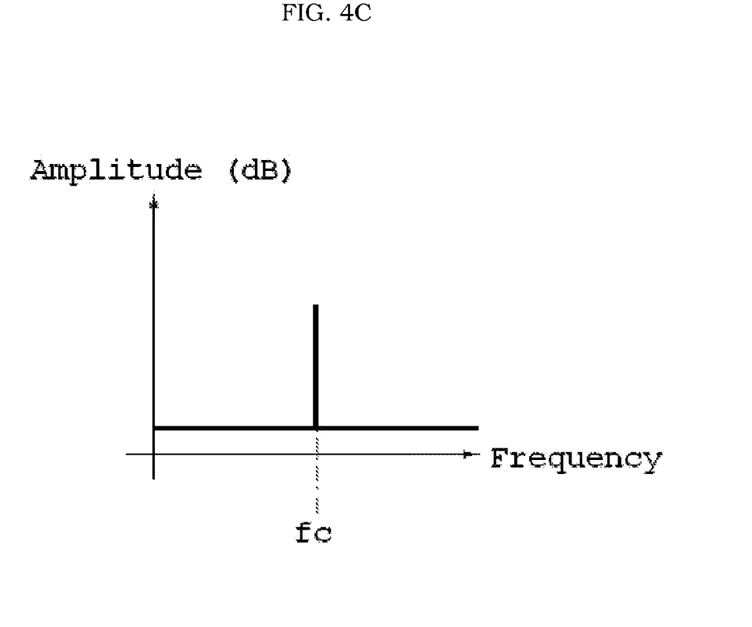

Referring again to FIG. 3, the second signal generator 20 may generate a second signal with a signal frequency corresponding to the center frequency of the wave generator 40 (S5). FIG. 4C illustrates the waveform of a second signal generated by the second signal generator 20. As illustrated, the second signal may be a signal having a frequency substantially equal to the center frequency fc of the wave generator 40.

Figure 4D:
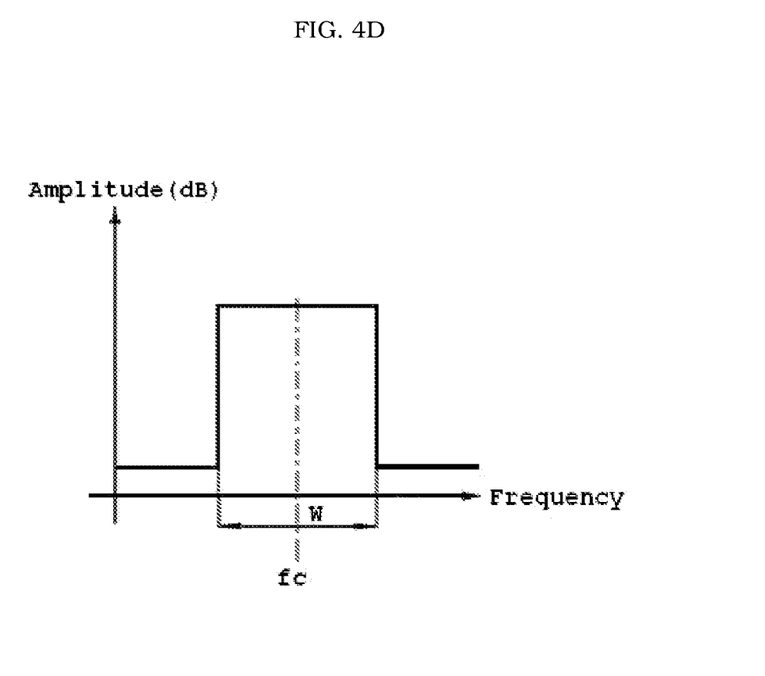

Once the first and second signals are generated, the signal blender 30 may blend the first signal with the second signal to create a blended signal (S6). FIG. 4D illustrates the waveform of a blended signal provided by the signal blender 30. As illustrated, the blended signal may have a bandwidth W substantially equal to the first signal with the second signal frequency fc as its center frequency, e.g., the frequency about which an equal amount of bandwidth is disposed on both sides.

According to an exemplary embodiment, the amplitude of the blended signal from the signal blender 30 may be amplified in the signal amplifier 31 (S7). In this case, the signal amplifier 31 may amplify the blended signal to an appropriate amplitude to be inputted to the wave generator 40 which is a SAW element.

The amplified, blended signal may be inputted to the wave generator 40. The wave generator 40 may generate a SAW using the input blended signal (S8). As described with reference to FIG. 2, the wave generator 40 may convert the blended signal, which is an electric signal, into a SAW through the input unit 41. The SAW may propagate through the reactor 43. The properties of the SAW may change depending on the characteristics of a substance bonded to the reactor 43. After going through the reactor 43, the SAW may be converted again into an electric signal in the output unit 42.

The signal detector 50 may detect an output signal from the wave generator 40 and compare it with an input signal, so as to sense the presence of a substance bonded to the reactor 43 of the wave generator 40 (S9). Moreover, the signal detector 50 may analyze any change in the center frequency, phase and signal amplitude of the output signal from the wave generator 40 to thus conduct quantitative and qualitative analysis of a target substance.

Figure 5A:
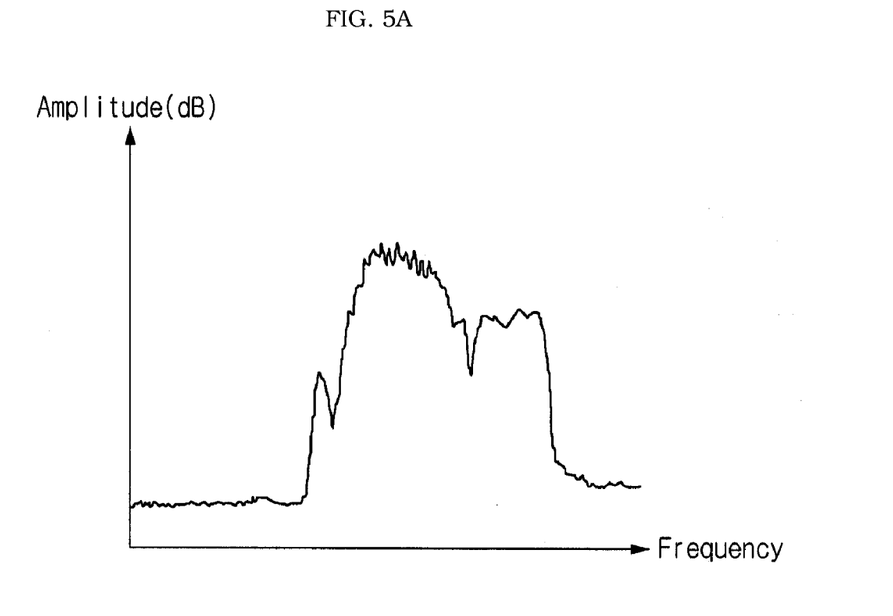
FIG. 5A is a graph illustrating an output signal waveform before a substance is bonded to an exemplary embodiment of a SAW sensor.
Figure 5B:
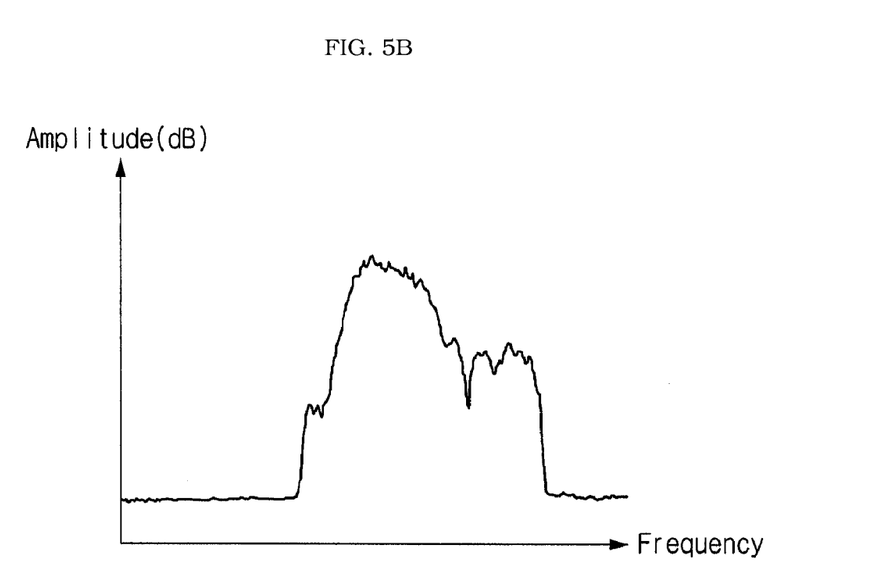
FIG. 5B is a graph showing an output signal waveform after a substance is bonded to an exemplary embodiment of a SAW sensor.

FIG. 5A and FIG. 5B show an output signal of an exemplary embodiment of a SAW sensor with respect to frequency.

FIG. 5A is a graph illustrating an output signal waveform when a substance is not bound onto the wave generator 40. On the other hand, FIG. 5B is a graph illustrating an output signal waveform when a substance is bound onto the wave generator 40. As illustrated in FIGS. 5A and 5B, the center frequency of an output signal and the frequency-dependent signal amplitude may be different before and after a target substance is bonded to the wave generator 40. These changes may be analyzed by the signal detector 50 to sense the presence of a substance bound onto the wave generator 40 and further, it may become possible to analyze the mass, pressure, density and/or viscosity, or other properties of the target substance.

While exemplary embodiments have been disclosed herein, it should be understood that other variations may be possible. Such variations are not to be regarded as a departure from the spirit and scope of example embodiments of the present application, and all such modifications as would be obvious to one skilled in the art are intended to be included within the scope of the following claims.

What is claimed is:

1. A surface acoustic wave sensor, comprising:
   a first signal generator which generates a first signal having a predetermined frequency bandwidth using a pseudo random sequence;
   a second signal generator which generates a second signal with a predetermined frequency;
   a signal blender which blends the first signal with the second signal to generate a blended signal having the predetermined frequency bandwidth with the predetermined frequency as a center frequency;
   a wave generator which generates a surface acoustic wave using the blended signal, which converts the surface acoustic wave into a third signal after the surface acoustic wave travels a predetermined distance, and which outputs the third signal; and a signal detector which detects a change in the third signal from the wave generator to sense a substance bound to the wave generator.

2. The surface acoustic wave sensor according to claim 1, wherein the wave generator comprises:
   an input unit which generates a surface acoustic wave using the blended signal;
   a reactor configured to bonding to the substance for analysis and which propagates the surface acoustic wave; and
   an output unit which converts the surface acoustic wave having passed through the reactor into the third signal and outputs the third signal.

3. The surface acoustic wave sensor according to claim 2, wherein:
   the output unit outputs different signals depending on characteristics of the substance bound to the reactor, and
   the frequency of the second signal is the center frequency of the third signal from the output unit when no substance is bound to the reactor.

4. The surface acoustic wave sensor according to claim 2, wherein the input unit and the output unit are interdigital transducers.

5. The surface acoustic wave sensor according to claim 1, wherein the signal detector detects a change in the third signal from the wave generator for analyzing at least one of mass, pressure, density and viscosity of the substance bound to the wave generator.

6. A sensing method using a surface acoustic wave, comprising:
   generating a first signal having a predetermined frequency bandwidth using a pseudo random sequence;
   generating a second signal with a predetermined frequency;
   blending the first signal with the second signal to generate a blended signal having the predetermined frequency bandwidth with the predetermined frequency as a center frequency;
   generating a surface acoustic wave using the blended signal in a wave generator;
   converting the surface acoustic wave into a third signal after the surface acoustic wave travels a predetermined distance along the wave generator;
   outputting the third signal from the wave generator; and
   detecting a change in the third signal from the wave generator to sense a substance bound to the wave generator.

7. The method according to claim 6, wherein:
   converting the surface acoustic wave into the third signal and outputting the third signal comprises outputting different signals depending on characteristics of the substance bound to the wave generator, and
   the frequency of the second signal is a center frequency of the third signal output in outputting the different signals when no substance is bound to the wave generator.

8. The method according to claim 6, further comprising:
   detecting a change in the third signal from the wave generator for analyzing at least one of mass, pressure, density and viscosity of the substance bound to the wave generator.

* * * * *